(12) United States Patent
Ide et al.

(10) Patent No.: US 8,158,729 B2
(45) Date of Patent: Apr. 17, 2012

(54) MATERIAL FOR PRODUCING BIOABSORBABLE MATERIAL, BIOABSORBABLE MATERIAL, AND PROCESS FOR PRODUCING THESE

(75) Inventors: Junichi Ide, Hiroshima (JP); Koichiro Toyota, Hiroshima (JP)

(73) Assignee: JMS Co., Ltd., Hiroshimashi (JP)

( * ) Notice: Subject to any disclaimer, the term of this patent is extended or adjusted under 35 U.S.C. 154(b) by 0 days.

(21) Appl. No.: 12/282,554

(22) PCT Filed: Mar. 14, 2007

(86) PCT No.: PCT/JP2007/055056
§ 371 (c)(1),
(2), (4) Date: Sep. 11, 2008

(87) PCT Pub. No.: WO2007/119352
PCT Pub. Date: Oct. 25, 2007

(65) Prior Publication Data
US 2009/0171036 A1 Jul. 2, 2009

(51) Int. Cl.
*C08G 63/91* (2006.01)

(52) U.S. Cl. ........ 525/415; 502/343; 525/410; 525/411; 525/450; 526/62; 585/906

(58) Field of Classification Search .................. 502/343; 525/450, 410, 411, 415; 526/62; 585/906
See application file for complete search history.

(56) References Cited

U.S. PATENT DOCUMENTS

| | | | | |
|---|---|---|---|---|
| 2,465,150 A | * | 3/1949 | Tennant | 528/262 |
| 2,465,319 A | * | 3/1949 | Whinfield et al. | 526/71 |
| 2,902,469 A | * | 9/1959 | Burkhard | 528/209 |
| 3,651,016 A | * | 3/1972 | Hrach et al. | 528/276 |
| 5,844,068 A | | 12/1998 | Otera et al. | |
| 6,350,812 B1 | | 2/2002 | Vert et al. | |
| 6,852,827 B2 | * | 2/2005 | Yamane et al. | 528/272 |
| 2007/0233275 A1 | * | 10/2007 | Shirahama et al. | 623/23.72 |

FOREIGN PATENT DOCUMENTS

| | | |
|---|---|---|
| JP | 10-218977 A | 8/1998 |
| JP | 2000-500803 A | 1/2000 |
| JP | 2000-191753 A | 7/2000 |
| JP | 2005-65771 A | 3/2005 |
| JP | 2006-182999 A | 7/2006 |
| WO | WO 2005/102404 * | 3/2005 |

OTHER PUBLICATIONS

Huang, M.H.; Li, S.; Coudane, J.; Vert, M.; Macromolecular Chemistry and Physics, 2003, vol. 204, p. 1994-2001.*
Sodergard, A.; Stolt, M.; Progress in Polymer Science, 2002 (27), p. 1123-1163.*
International Search Report of PCT/JP2007/055056, date of mailing May 22, 2007.

* cited by examiner

*Primary Examiner* — David W Wu
*Assistant Examiner* — Robert Jones, Jr.
(74) *Attorney, Agent, or Firm* — Westerman, Hattori, Daniels & Adrian, LLP (57) ABSTRACT

[PROBLEMS]
To provide a material for producing a bioabsorbable material in which it is easy to remove a metal zinc catalyst from a bioabsorbable polymer such as a polymer of lactide or a polymer of lactide and caprolactone and it is easy to recycle the removed powdery metal zinc catalyst, and to provide a bioabsorbable material produced from the material for producing a bioabsorbable material.
[MEANS FOR SOLVING PROBLEMS]
A material for producing a bioabsorbable material including a three-dimensionally shaped metal zinc polymerization catalyst and a bioabsorbable polymer such as a polymer of lactide or a polymer of lactide and caprolactone; and a process for producing a material for producing a bioabsorbable material, characterized in that in the process for producing a bioabsorbable polymer by polymerization, a three-dimensionally shaped metal zinc catalyst is used as a polymerization catalyst.

3 Claims, 7 Drawing Sheets

MATERIAL FOR PRODUCING BIOABSORBABLE MATERIAL, BIOABSORBABLE MATERIAL, AND PROCESS FOR PRODUCING THESE

TECHNICAL FIELD

The present invention relates to a material for producing a bioabsorbable material, a bioabsorbable material and processes for producing these materials.

BACKGROUND ART

It is a fact well known in the art that a bioabsorbable material formed of a bioabsorbable polymer such as a polymer obtained by polymerizing lactide or by polymerizing lactide and caprolactone is used as a cell scaffold material in the field of regenerative therapy. Additionally, when bioabsorbable polymers are produced by polymerization, tin compounds excellent in catalytic activity such as tin octylate are often used as catalysts. It is to be noted that the afore-mentioned tin compound offers a problem of the toxicity to living organisms. For the purpose of solving this problem, there have been proposed the use of metal zinc lower in the toxicity to living organisms as compared to the aforementioned tin compound and the use of powdery metal zinc as the polymerization catalyst for the polymerization of lactide or caprolactone polymer which is a bioabsorbable polymer (Non-Patent Documents 1 and 2).

Non-Patent Document 1: Polymer International 46, 177 (1998)

Non-Patent Document 2: J Biomed Mater Res 69A, 417 (2004)

DISCLOSURE OF THE INVENTION

Problems to be Solved by the Invention

A bioabsorbable material, such as a bioabsorbable material formed of a bioabsorbable polymer obtained by polymerizing lactide or by polymerizing lactide and caprolactone by using powdery metal zinc as a polymerization catalyst, undergoes the adverse mixing of the metal zinc catalyst in the bioabsorbable polymer because of the use of the powdery catalyst as the polymerization catalyst. It is extremely difficult to remove the metal zinc catalyst adversely mixed in the bioabsorbable polymer from the bioabsorbable polymer. In other words, it is difficult to remove the metal zinc catalyst from the bioabsorbable polymer, and the recycle of the used metal zinc catalyst has taken a lot of time and labor. Further, the powdery metal zinc catalyst has also suffered from a problem of being low in the catalytic activity thereof as well as the problem of being difficult in recycling.

The present invention resides in the provision of a material for producing a bioabsorbable material which solves the above-described technical problems, a bioabsorbable material and processes for producing these materials.

Means for Solving the Problems

A first aspect of the present invention has been able to solve the above-described technical problems by providing a material for producing a bioabsorbable material, the material for producing a bioabsorbable material being produced by polymerization using as a polymerization catalyst a three-dimensionally shaped metal zinc catalyst, and by providing a process for producing the material for producing a bioabsorbable material.

The three-dimensionally shaped metal zinc catalyst as referred to above signifies a catalyst having a three-dimensional shape other than a powdery shape and a granular shape, and additionally has the following properties:

(1) the shape of the three-dimensionally shaped metal zinc catalyst is a shape enabling the concerned catalyst to be separated from the produced bioabsorbable polymer by physical force means such as by peeling-off means or by cutting-off means;

(2) the bioabsorbable polymer attached to a portion of the separated three-dimensionally shaped metal zinc catalyst can be easily removed by washing and the catalyst concerned can be easily recycled as a catalyst; and (3) the three-dimensionally shaped metal zinc catalyst can be widely located all over the reaction system and dose not disturb the stirring of the reaction system during polymerization.

Examples of the three-dimensional shape satisfying the above-described properties include a linear shape such as a wire-like shape, a rod-like shape, a plate-like shape, a ball-like shape, a net-like shape and a mesh-like shape; particularly preferable among these are the wire-like shape, the rod-like shape and the plate-like shape. As the size of the three-dimensionally shaped metal zinc catalyst to be located in the reaction system, there may be quoted a size with which the surface area of the three-dimensionally shaped metal zinc catalyst is allowed to be approximately the same as the total surface area of the metal zinc catalyst at the time of being used in a powdery shape; however, the present invention is not limited to this quoted example.

The bioabsorbable polymer produced by the polymerization using the heretofore known metal zinc powder catalyst necessitates purification means for removing the metal zinc powder from the concerned polymer. As such means, there may be quoted, for example, means in which the obtained bioabsorbable polymer is dissolved in a solvent such as dichloromethane, the metal zinc powder catalyst is removed by filtration from the solution thus obtained, and thereafter reprecipitation of the bioabsorbable polymer into ethanol is conducted. However, such purification means takes extremely a lot of time and labor. In contrast to this, in the bioabsorbable material of the present invention, only by removing, from the material for producing a bioabsorbable material, the three-dimensionally shaped metal zinc catalyst portion by applying physical force such as by peeling off or by cutting off, the metal zinc catalyst content in the bioabsorbable material can be made to be an extremely small amount, for example, 100 ppm or less, and further 60 ppm or less, for example, 20 to 60 ppm. Accordingly, the bioabsorbable material of the present invention can be used as it is, as a bioabsorbable material even without applying such purification means as described above. For example, the polymer after removal of the three-dimensionally shaped metal zinc catalyst portion from the material for producing a bioabsorbable material is chipped without applying any purification to remove the metal zinc catalyst, and the chip thus obtained is molded into an intended shape such as a film-like shape so as to be usable.

A second aspect of the present invention has been able to provide a bioabsorbable material which solves the above-described technical problems by using as the reactor a reactor in which at least part of the inner wall surface is formed of metal zinc, in place of or together with the three-dimensionally shaped metal zinc catalyst.

As for the reactor, the reactor itself may be formed of metal zinc, or the reactor itself is formed of a metal other than metal zinc and at least part of the inner surface of the reactor may be formed of a metal zinc layer. Examples of the means for forming the metal zinc layer include plating means. The bioabsorbable polymer obtained by using such a reactor formed of metal zinc can also be used as a bioabsorbable material as it is without being subjected to any purification.

The type and the polymerization method of the bioabsorbable polymer constituting the bioabsorbable material of the present invention are not particularly limited, and heretofore known types and methods may be used; however, typically the aforementioned polymer of lactide or the aforementioned polymer of lactide and caprolactone may be quoted. The polymer of lactide and caprolactone may be prepared by copolymerizing lactide and caprolactone as the starting materials through ring-opening polymerization, or lactide (cyclic dimmer of lactic acid) may be synthesized from lactic acid and then the lactide may be copolymerized with caprolactone. As the lactide, L-lactide, D-lactide and a mixture (D,L-lactide) thereof can be used, and as lactic acid, L-lactic acid, D-lactic acid and a mixture (D,L-lactic acid) thereof can be used. Additionally, as the lactone, for example, ε-caprolactone, γ-butyrolactone and δ-valerolactone are quoted. The polymer of lactide or the polymer of lactide and caprolactone may also be those polymers which contain, as the constituent components, copolymerization components constituting other bioabsorbable polymers, other than lactide and caprolactone. Examples of such copolymerization components may include those copolymerization components derived from glycolic acid, trimethylene carbonate, β-hydroxybutyric acid, proteins and sugars. Further, examples of the bioabsorbable polymer obtained by using the three-dimensionally shaped metal zinc catalyst include polyglycolic acid, glycolic acid-trimethylene carbonate copolymer and poly-β-hydroxybutyric acid as well as the polymer of lactide or the polymer of lactide and caprolactone.

BEST MODE OF CARRYING OUT THE INVENTION

Example 1

In a glass test tube-shaped polymerization tube of 18 mm in diameter and 180 mm in length, 5 g of L-lactide (LA), an equimolar amount of ε-caprolactone and lauryl alcohol as a polymerization initiator in an amount of 200 (mol ppm) in relation to the monomers were placed. In the polymerization tube, there was added as a polymerization catalyst one string (the surface area $3.0 \times 10^{-4}$ cm$^2$) of metal zinc wire (purity: 99% or more) of 1 mm in diameter and 30 mm in length, beforehand subjected to a hydrochloric acid treatment to remove the oxide coating film. The contents of the polymerization tube were dehydrated under a reduced pressure for 16 hours, and thereafter the polymerization tube was sealed. Polymerization was conducted in an oil bath set at 140° C. under stirring for each of the following periods of time: 24, 48, 72, 96 and 120 hours. After polymerization, the polymerization tube was immersed in liquid nitrogen to be broken, then the polymer and the broken glass were separated from each other, and then the polymer was cut into 2-mm cubes and the portion formed of the metal zinc wire was removed. The thus removed metal zinc wire was washed with dichloromethane and recycled as a catalyst. The solid polymerization product with the metal zinc wire removed therefrom was twice washed with ethanol in an amount of approximately 10 times (by weight) the amount of the polymer, and subjected to vacuum drying for at least 5 days with a vacuum pump. For each of the polymers thus obtained, the polymerization percentage, the weight average molecular weight, the LA content and the residual zinc amount in the polymer are shown in Table 1 as Example. Each of the polymerization percentages was obtained from the weights of the monomers before purification and the weight of the polymer after purification. Additionally, the molecular weights were obtained by means of GPC, and the contents of L-lactide and ε-caprolactone were measured by means of $^1$H-NMR.

Comparative Example 1

Polymerization was conducted in the same manner as in Example 1, except that: in place of the metal zinc wire used as the catalyst in above Example 1, a metal zinc power catalyst (purity: 99% or more) having the same surface area, based on calculation, as that of the metal zinc wire was used; and each of the obtained solid polymerization products was dissolved in dichloromethane, the solution thus obtained was filtered to remove the metal zinc powder catalyst, and thereafter each of the solid polymerization products was collected. For each of the solid polymerization products obtained by this polymerization, the polymerization percentage, the weight average molecular weight, the LA content and the residual zinc amount in the polymer are shown in Table 2 as Comparative Example.

TABLE 1

| Reaction time (hr) | Polymerization percentage (%) | Mw ave | Mw SD | LA content (%) ave | LA content (%) SD | Residual zinc amount in polymerization product (wt · ppm) |
|---|---|---|---|---|---|---|
| 24 | 44.5 | 104,000 | 3,000 | 88.4 | 0.2 | 29.6 |
| 48 | 75.5 | 132,000 | 5,000 | 70.8 | 0.5 | 72.2 |
| 72 | 87.3 | 124,000 | 5,000 | 59.6 | 0.8 | 57.1 |
| 96 | 92.5 | 74,000 | 3,000 | 55.2 | 0.3 | 54.6 |
| 120 | 87.0 | 111,000 | 6,000 | 60.4 | 3.2 | 53.2 |

TABLE 2

| Reaction time (hr) | Polymerization percentage (%) | MW ave | MW SD | LA content (%) ave | LA content (%) SD | Residual zinc amount in polymerization product (wt · ppm) |
|---|---|---|---|---|---|---|
| 24 | 9.3 | 73000 | 1528 | 94.1 | 0.7 | 83.2 |
| 48 | 52.5 | 219000 | 6110 | 86.3 | 0.2 | 72.8 |
| 72 | 68.0 | 261000 | 3786 | 85.4 | 0.2 | 95.6 |
| 96 | 61.0 | 259000 | 2082 | 87.4 | 0.3 | 82.6 |

Example 2

Two strings of the same metal zinc wire of 1 mm in diameter and 30 mm in length as used in Example 1 were used as the polymerization catalyst. The results thus obtained are shown in Table 3 presented below.

TABLE 3

| Reaction time (hr) | Polymerization percentage (%) | Mw ave | Mw SD | LA content (%) ave | LA content (%) SD | Residual zinc amount in polymerization product (wt · ppm) |
|---|---|---|---|---|---|---|
| 24 | 56.5 | 171,000 | 20,000 | 88.4 | 1.1 | 65.8 |
| 48 | 87.5 | 68,000 | 0 | 70.8 | 1.9 | 54.1 |
| 72 | 95.8 | 134,000 | 9,000 | 59.6 | 0.2 | 82.8 |
| 96 | 96.3 | 163,000 | 5,000 | 55.2 | 2.1 | 61.3 |
| 120 | 95.0 | 181,000 | 3,000 | 60.4 | 2.6 | |

Example 3

Figure 1:
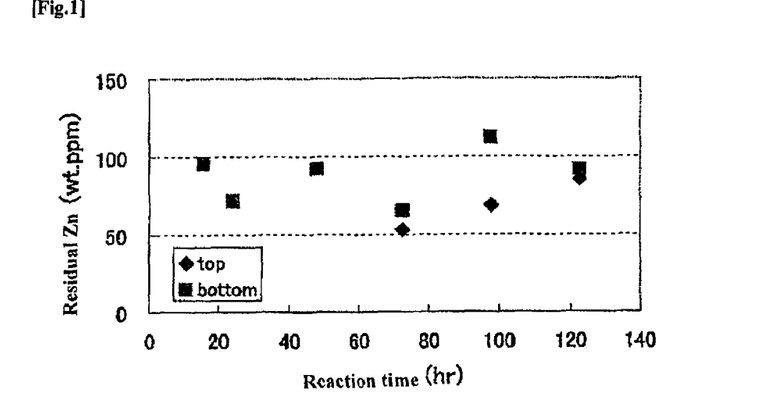
FIG. 1 is a graph showing the residual zinc amounts at the top part and the bottom part of the polymer prepared by using one sheet of metal zinc plate.

In place of the one string of metal zinc wire of 1 mm in diameter and 30 mm in length used in Example 1, one sheet (surface area: $1.6 \times 10^{-4}$ cm$^2$) of metal zinc plate (purity: 99% or more) of 5 mm in width, 30 mm in length and 0.3 mm in thickness was used as the polymerization catalyst. The results thus obtained are shown in Table 4 presented below. Additionally, the results of a comparison between the residual zinc amount in the top part and the residual zinc amount in the bottom part are shown in FIG. 1. It is to be noted that in a polymerization product obtained by using a metal zinc plate as the polymerization catalyst, the zinc plate sinks in the lower part of the polymerization product, and hence the polymerization product is divided into the upper and lower parts with a boundary set so as to be midway between the upper and lower parts, and the former part is referred to as the top part and the latter part is referred to as the bottom part.

TABLE 4

| Reaction time (hr) | top/bottom | Polymerization percentage (%) | Mw ave | Mw SD | LA content (%) ave | LA content (%) SD | Residual zinc amount in polymerization product (wt · ppm) |
|---|---|---|---|---|---|---|---|
| 15 | — | 22.3 | 72,000 | 2,309 | 93.4 | 0.7 | 95.6 |
| 24 | — | 52.1 | 115,000 | 26,764 | 86.0 | 0.1 | 71.8 |
| 48 | top | 72.9 | 136,000 | 1,528 | 68.5 | 1.1 | — |
| | bottom | 84.7 | 128,000 | 7,638 | 69.6 | 1.6 | 91.8 |
| 72 | top | 62.3 | 176,000 | 7,937 | 80.8 | 1.6 | 53.8 |
| | bottom | 72.2 | 164,000 | 3,215 | 80.4 | 1.5 | 65.8 |
| 96 | top | 87.8 | 164,000 | 5,508 | 53.5 | 2.4 | 68.7 |
| | bottom | 94.4 | 176,000 | 2,646 | 65.8 | 2.2 | 112.2 |
| 120 | top | 94.3 | 140,000 | 577 | 51.4 | 1.3 | 85.5 |
| | bottom | 95.8 | 152,000 | 3,512 | 54.9 | 0.5 | 91.6 |

It is to be noted herein that in the table presented above, each of the polymers associated with the reaction times of 15 and 24 hours was not an "agglomerate" in a manner precluding the separation into the "top" and "bottom" parts, and hence, after the polymerization treatment, the polymerization product was subjected to a reprecipitation treatment with dichloromethane to precipitate the polymer so as to yield the measurement sample.

Example 4

Figure 2:
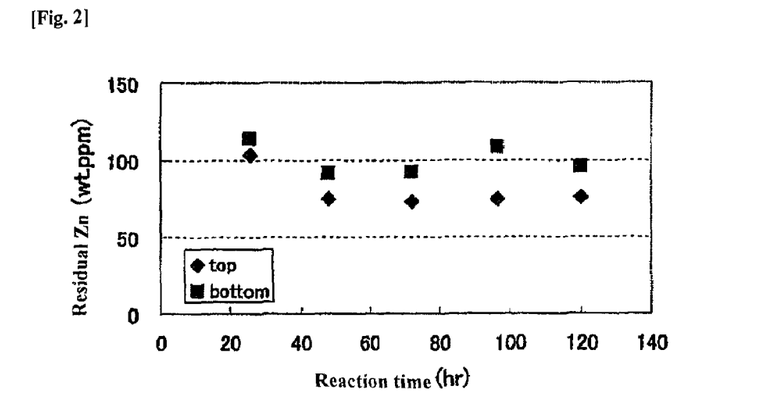
FIG. 2 is a graph showing the residual zinc amounts at the top part and the bottom part of the polymer prepared by using two sheets of metal zinc plate.

In place of the one string of metal zinc wire of 1 mm in diameter and 30 mm in length used in Example 1, two sheets (surface area: $3.2 \times 10^{-4}$ cm$^2$) of metal zinc plate of 5 mm in width, 30 mm in length and 0.3 mm in thickness was used as the polymerization catalyst to conduct polymerization to prepare a bioabsorbable polymer. The results thus obtained are shown in Table 5 presented below. Additionally, the results of a comparison between the residual zinc amount in the top part and the residual zinc amount in the bottom part are shown in FIG. 2.

TABLE 5

| Reaction time (hr) | top/ bottom | Polymerization percentage (%) | Mw ave | Mw SD | LA content (%) ave | LA content (%) SD | Residual zinc amount in polymerization product (wt · ppm) |
|---|---|---|---|---|---|---|---|
| 24 | top | 77.4 | 186,000 | 3,786 | 67.3 | 1.3 | 103.7 |
|    | bottom | 83.4 | 182,000 | 3,464 | 63.4 | 2.0 | 114.2 |
| 48 | top | 86.3 | 221,000 | 6,506 | 59.4 | 1.0 | 75.0 |
|    | bottom | 92.3 | 221,000 | 2,646 | 59.8 | 0.2 | 91.2 |
| 72 | top | 93.1 | 210,000 | 6,807 | 54.0 | 1.0 | 73.1 |
|    | bottom | 95.4 | 224,000 | 3,512 | 56.9 | 1.0 | 91.9 |
| 96 | top | 94.6 | 224,000 | 3,512 | 54.1 | 0.4 | 75.4 |
|    | bottom | 95.8 | 242,000 | 4,933 | 54.3 | 0.6 | 108.7 |
| 120 | top | 95.6 | 269,000 | 2,000 | 52.0 | 1.3 | 75.9 |
|    | bottom | 96.3 | 274,000 | 3,512 | 54.0 | 2.1 | 95.3 |

Example 5

Figure 12:
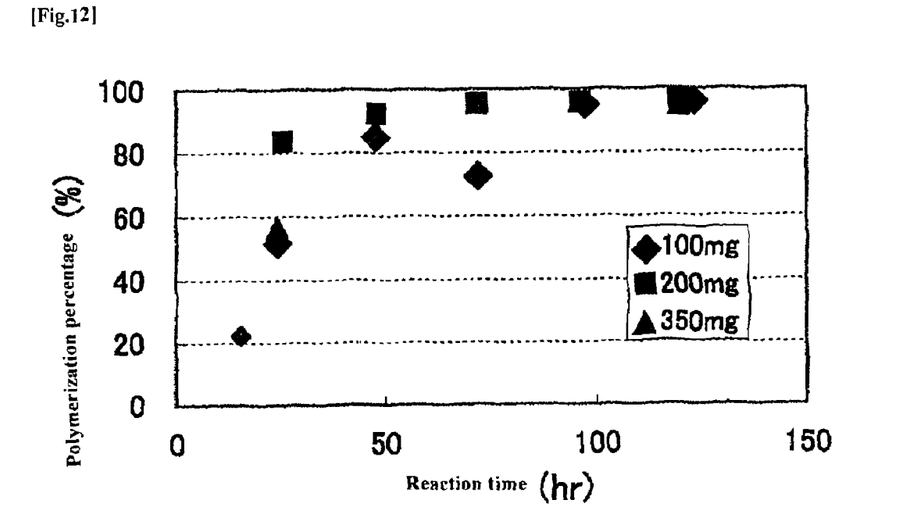
FIG. 12 is a graph showing the polymerization percentages (%) in the cases where polymerization was conducted by using respectively two strings (350 mg) of metal zinc wire, and one sheet (100 mg) and two sheets (200 mg) of metal zinc plate.

Polymerization was conducted in the same manner as in Example 1, except that in place of one string of metal zinc wire, two strings (350 mg) of the above-described wire, one sheet (100 mg) of the above-described plate and two sheets (200 mg) of the above-described plate were separately used. The polymerization percentages thus obtained are shown in FIG. 12.

Test results of Examples 1 to 5 and Comparative Example 1.

1. As can be seen from the experimental results of Example 1 shown in Table 1 presented above and the experimental results of Comparative Example 1 shown in Table 2 presented above, the bioabsorbable polymers shown in Table 1, using as the polymerization catalyst one string of metal zinc wire are larger in the polymerization percentage than the bioabsorbable polymers of Comparative Example 1 shown in Table 2, using as the polymerization catalyst the metal zinc powder having the surface area of the same order of magnitude as the surface area of the one string of metal zinc wire; and accordingly, the one string of metal zinc wire is higher in the activity as the polymerization catalyst than the metal zinc powder. In addition to this higher catalytic activity, the bioabsorbable polymer shown in Table 1, prepared by using metal zinc wire is lower in the amount of the zinc remaining in the bioabsorbable polymer in such an order of magnitude that the bioabsorbable polymer can be used as it is as a bioabsorbable material, without applying any purification treatment in contrast to the bioabsorbable polymer of Comparative Example 1, prepared by using the metal zinc powder, being in need of application of some sort of purification treatment.

2. In each of the bioabsorbable polymers shown in Table 2 presented above, $\epsilon$-caprolactone was scarcely involved in the reaction, but in each of the bioabsorbable polymers shown in Table 1 presented above, the content of $\epsilon$-caprolactone is higher than those of the bioabsorbable polymers shown in Table 2, and the copolymerized amount of $\epsilon$-caprolactone can be made large. Accordingly, it is possible to make smaller the usage amount of $\epsilon$-caprolactone required for production of a copolymer of L-lactide (LA) and $\epsilon$-caprolactone, copolymerized so as to have an intended copolymerization amount of $\epsilon$-caprolactone.

Figure 3:
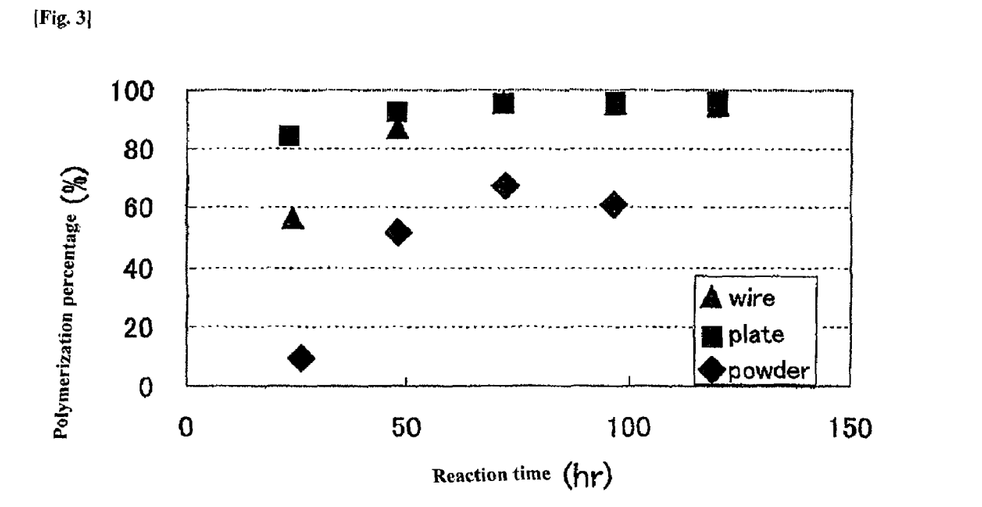
FIG. 3 is a graph showing the polymerization percentages in the cases respectively using two strings of metal zinc wire, two sheets of metal zinc plate and a metal zinc powder.
Figure 4:
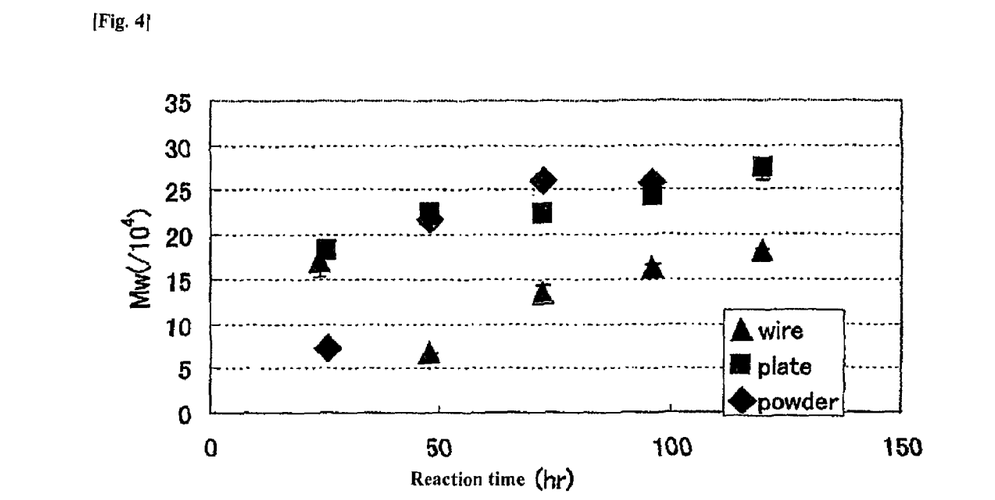
FIG. 4 is a graph showing the molecular weights (Mws) of the polymers prepared by using respectively two strings of metal zinc wire, two sheets of metal zinc plate and a metal zinc powder.
Figure 5:
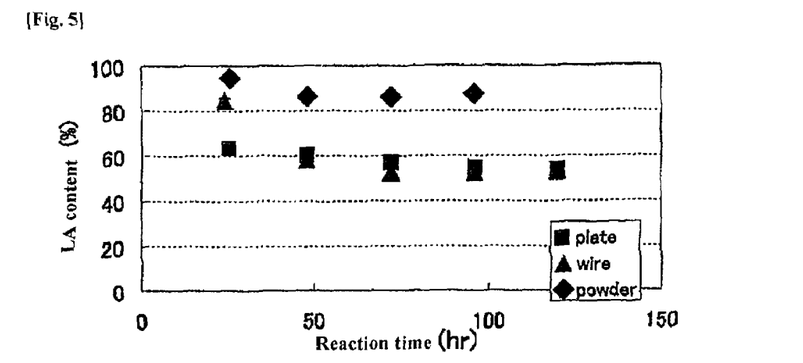
FIG. 5 is a graph showing the LA contents (%) in the polymers prepared by using respectively two strings of metal zinc wire, two sheets of metal zinc plate and a metal zinc powder.
Figure 6:
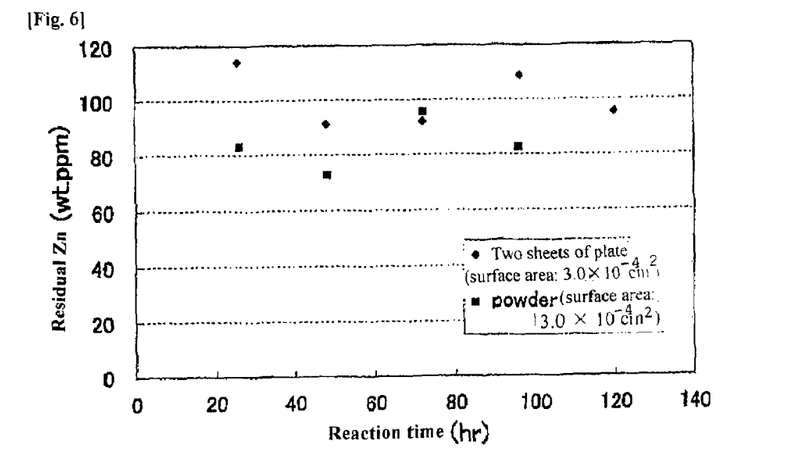
FIG. 6 is a graph showing the residual Zn amounts (wt. ppm) in the polymers prepared by using respectively two sheets of metal zinc plate and a metal zinc powder having the same surface area as that of the two sheets of metal zinc plate.
Figure 7:
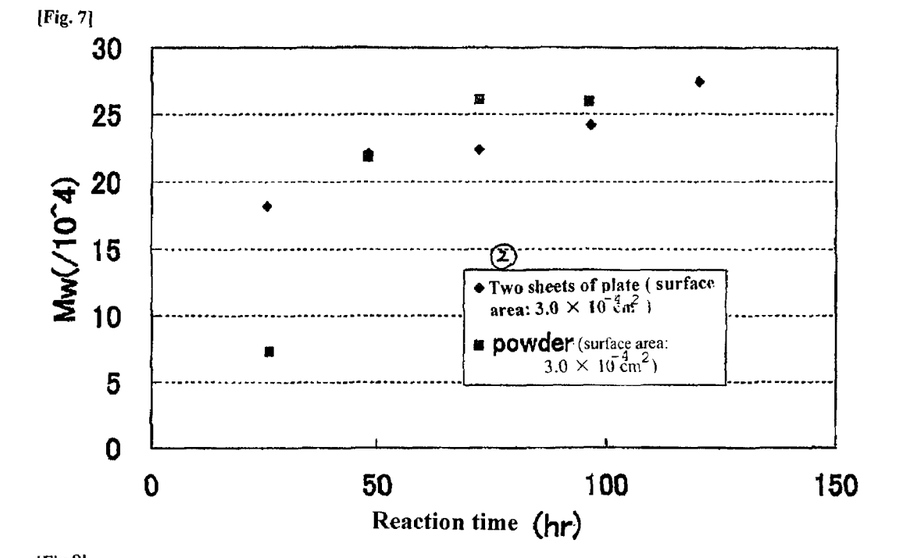
FIG. 7 is a graph showing the molecular weights (Mws) of the polymers prepared by using respectively two sheets of metal zinc plate and a metal zinc powder having the same surface area as that of the two sheets of metal zinc plate.
Figure 8:
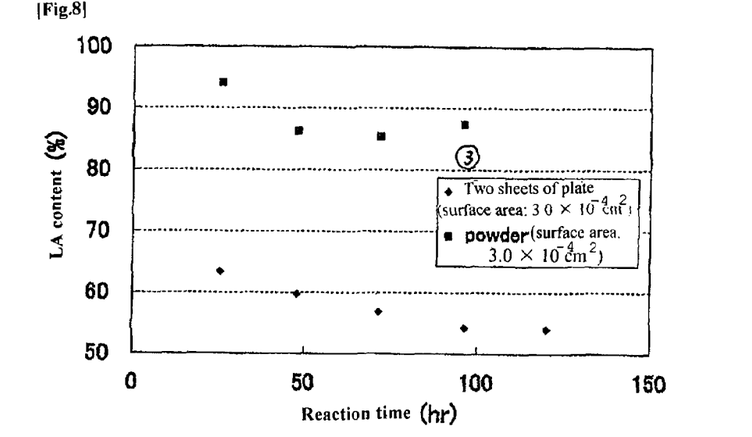
FIG. 8 is a graph showing the LA contents (%) in the polymers prepared by using respectively two sheets of metal zinc plate and a metal zinc powder having the same surface area as that of the two sheets of metal zinc plate.
Figure 9:
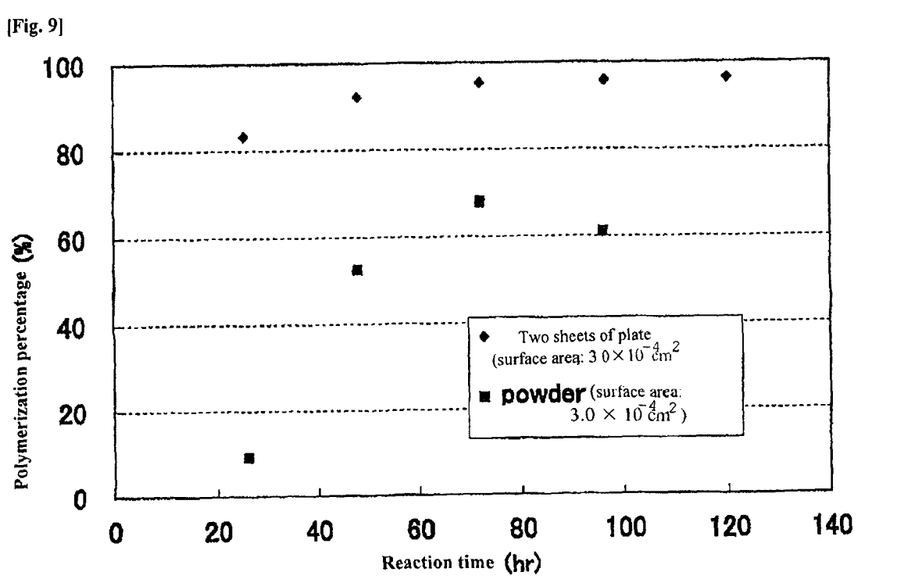
FIG. 9 is a graph showing the polymerization percentages (%) of the polymers prepared by using respectively two sheets of metal zinc plate and a metal zinc powder having the same surface area as that of the two sheets of metal zinc plate.

3. As can be seen from FIG. 3 showing the polymerization percentages and FIG. 5 showing the LA contents of Comparative Example 1, Example 2 and Example 4 using the metal zinc powder, the two strings of metal zinc wire and the two sheets of metal zinc plate, respectively, all having the surface areas of the same order of magnitude, the metal zinc wire and the metal zinc plate are higher in activity than the metal zinc powder in the same manner as in the above description 1, and the $\epsilon$-caprolactone contents (%) are higher with the metal zinc wire and the metal zinc plate than with the metal zinc powder.

Figure 10:
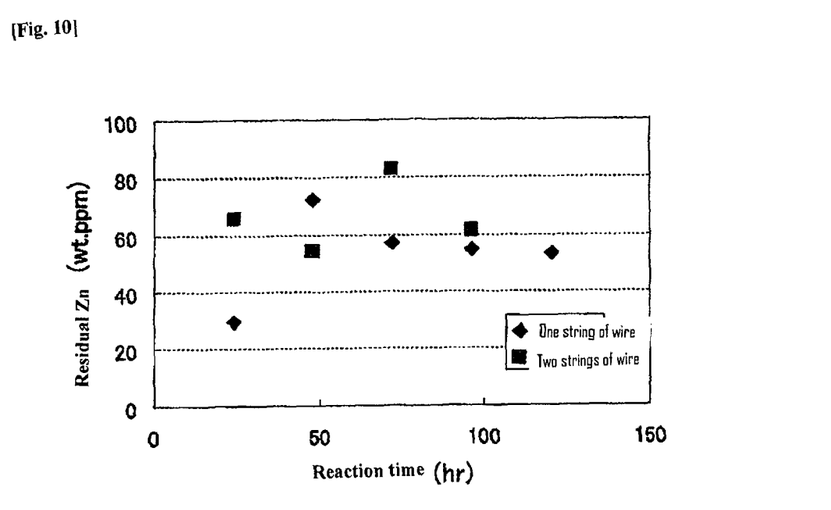
FIG. 10 is a graph showing the residual Zn amounts (wt. ppm) in the polymers prepared by using respectively one string of metal zinc wire and two strings of metal zinc wire.

4. As can be seen from the results of FIG. 10 showing the residual Zn amounts in the bioabsorbable polymers of Examples 1 and 2, respectively, using one and two strings of metal zinc wire, the residual Zn amount in the bioabsorbable polymer is not affected by the total area of the wire-shaped metal zinc in the cases where wire-shaped metal zinc is used.

Figure 11:
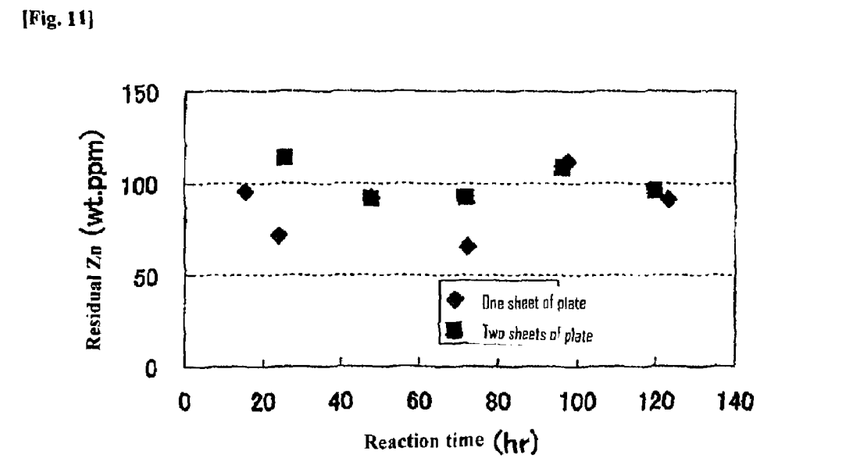
FIG. 11 is a graph showing the residual Zn amounts (wt. ppm) in the polymers prepared by using respectively one sheet of metal zinc plate and two sheets of metal zinc plate.

5. As can be seen from the results of FIG. 11 showing the residual Zn amounts in the bioabsorbable polymers of Examples 3 and 4, respectively, using one and two sheets of metal zinc plate, the residual Zn amount in the bioabsorbable polymer is not affected by the total area of the plate-shaped metal zinc in the cases where plate-shaped metal zinc is used.

6. As can be seen from FIG. 12 showing the polymerization percentages in Example 5, in the cases where metal zinc plate and metal zinc wire are used, the weights of these catalysts substantially do not affect the polymerization percentages.

As can be seen from these results, as for the polymerization catalyst in the polymerization process of the bioabsorbable polymer, three-dimensionally shaped catalysts made of metal zinc such as metal zinc wire and metal zinc plate are higher in catalytic activity than a metal zinc powder catalyst, and the polymer with the three-dimensionally shaped catalyst physically removed therefrom does not need a separate step of removing the catalyst and is high in usefulness.

Example 6

Figure 13:
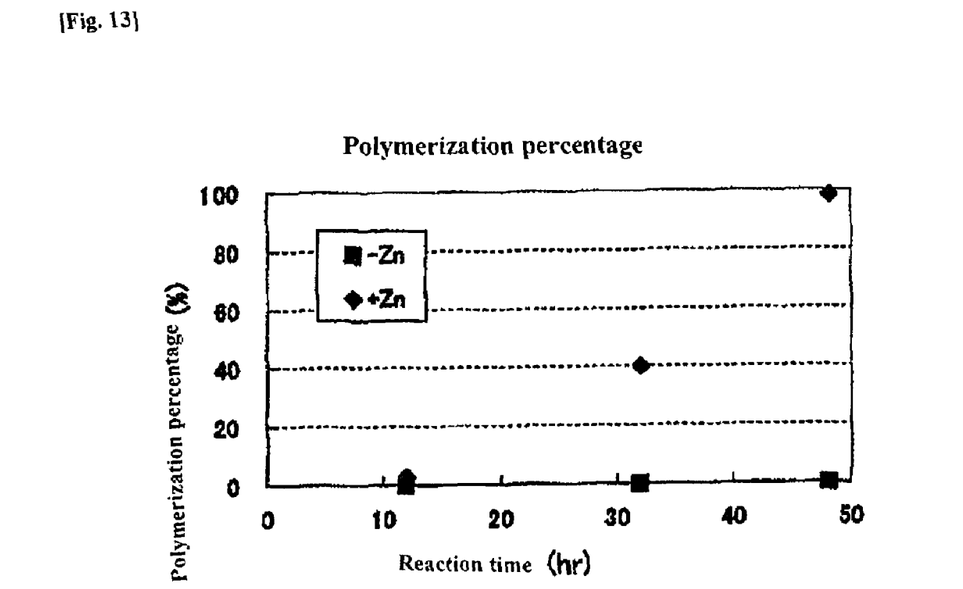
FIG. 13 is a graph showing the polymerization percentage in the case where polymerization of ε-caprolactone (CL) was conducted by using two sheets of the metal zinc plate of Example 5.
Figure 14:
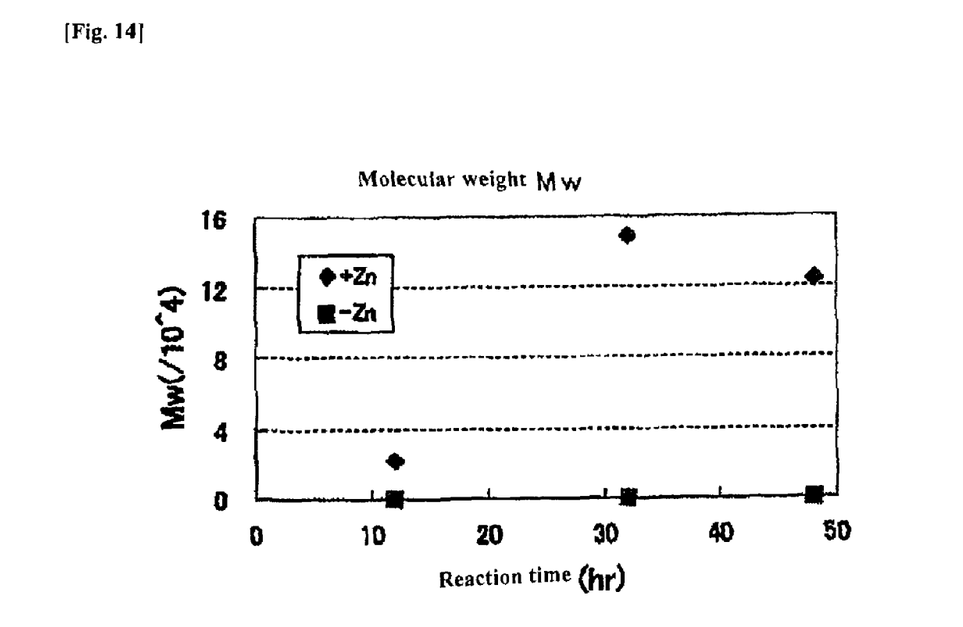
FIG. 14 is a graph showing the molecular weight (Mw) of the polymer in the case where polymerization of ε-caprolactone (CL) was conducted by using two sheets or the metal zinc plate of Example 6.

In a glass test tube-shaped polymerization tube of 18 mm in diameter and 180 mm in length, 8 ml of $\epsilon$-caprolactone (CL) and lauryl alcohol as a polymerization initiator in an amount of 200 (mol ppm) in relation to the s-caprolactone monomer were placed. In the polymerization tube, there was added as a polymerization catalyst two sheets of metal zinc plate of 15 mm in width, 30 mm in length and 0.3 mm in thickness, beforehand subjected to a hydrochloric acid treatment to remove the oxide coating film. Polymerization operation was conducted to prepare poly($\epsilon$-caprolactone) (PCL) in the same manner as in Example 1 for each of the following polymerization reaction times: 12, 32 and 48 hours. Additionally, for comparison, the same polymerization operation was conducted without using the above-described polymerization catalyst. The results thus obtained are shown in Table 6 presented below and FIGS. 13 and 14.

TABLE 6

|  | Reaction time (hr) | Polymerization percentage (%) | Mw |
|---|---|---|---|
| −Zn | 12 | n.d. | n.d. |
|  | 32 | n.d. | n.d. |
|  | 48 | n.d. | n.d. |
| +Zn | 12 | 3.0 | 22000 |
|  | 32 | 40.5 | 149000 |
|  | 48 | 98.3 | 124000 |

In the table presented above, the test results under the heading of −Zn represent the results for the cases where no metal zinc plate was made present, and the results under the heading of +Zn represent the results for the cases where metal zinc plate was made present. As can be seen from these results, in the preparation of poly(ε-caprolactone), the metal Zinc plate attains catalytic effects.

Example 7

Figure 15:
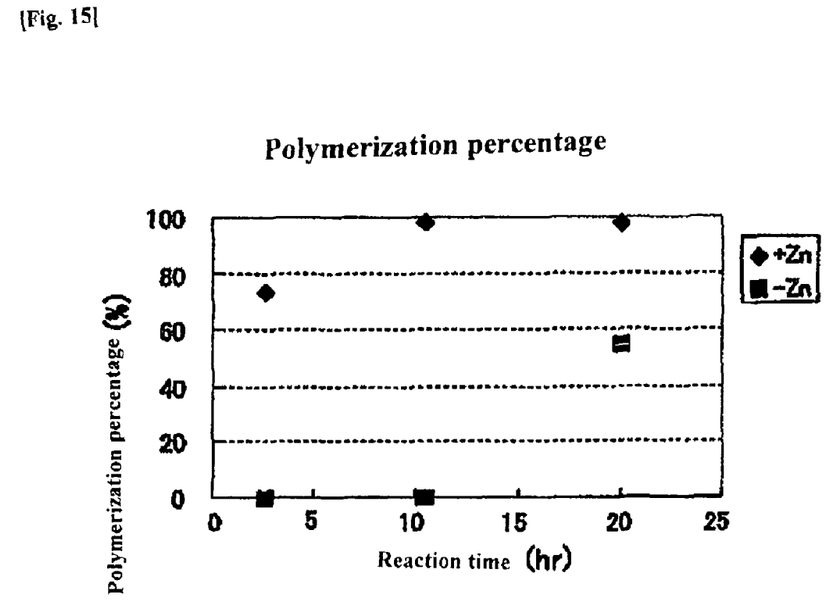
FIG. 15 is a graph showing the polymerization percentage in the case of Example 7 where polymerization of trimethylene carbonate (TMC) was conducted.
Figure 16:
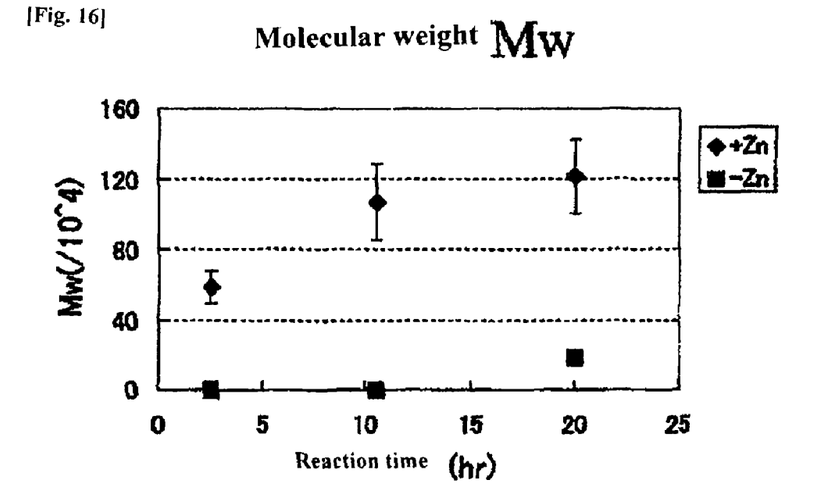
FIG. 16 is a graph showing the molecular weight (Mw) of the polymer in the case of Example 7 where polymerization of trimethylene carbonate (TMC) was conducted.

Polymerization of trimethylene carbonate (TMC) was conducted in the same manner as in Example 6 except that 7.5 g of trimethylene carbonate (TMC) was adopted in place of ε-caprolactone and the polymerization reaction times of 2.5, 10.5 and 20 hours were adopted. Additionally, similarly to the case of Example 5, for comparison, polytrimethylene carbonate (PTMC) was prepared without using the polymerization catalyst by applying the same polymerization operations. The results thus obtained are shown in Table 7 presented below and FIGS. 15 and 16. Among these results, in the test results for −Zn (a case where no polymerization catalyst was used), a reaction time of 20 hours also enabled a preparation of the polymer. However, in the test results for +Zn (a case where a polymerization catalyst was used), the same reaction time of 20 hours yielded a polymer, polytrimethylene carbonate (PTMC), having a relatively higher molecular weight of the order of $10^6$. As can be seen from the above results, the metal zinc plate attains catalytic effects in the preparation of polytrimethylene carbonate (PTMC).

TABLE 7

|  | Reaction time (hr) | Polymerization percentage (%) | Mw |
| --- | --- | --- | --- |
| −Zn | 2.5 | n.d. | n.d. |
|  | 10.5 | n.d. | n.d. |
|  | 20 | 55.1 | 182000 |
| +Zn | 2.5 | 73.5 | 588000 |
|  | 10.5 | 98.4 | 1070000 |
|  | 20 | 97.8 | 1214000 |

The residual zinc amounts in the PCL obtained in Example 5 and the residual zinc amounts in the PTMC obtained in Example 6 are shown in Tables 8 and 9 presented below, respectively.

TABLE 8

| PCL | | |
| --- | --- | --- |
| Reaction time (hr) | Polymerization percentage (%) | Zn (wt. ppm) |
| 12 | 3.0 | 680.9 |
| 32 | 40.5 | 229.6 |
| 48 | 98.3 | 337.7 |

TABLE 9

| PTMC | | |
| --- | --- | --- |
| Polymerization percentage (%) | Polymerization percentage (%) | Zn (wt. ppm) |
| 2.5 | 73.5 | 4.1 |
| 10.5 | 98.4 | 3.8 |
| 20 | 97.8 | 1.5 |

INDUSTRIAL APPLICABILITY (1) The present invention adopts as the shape of the catalyst a three-dimensional shape when a material for producing a bioabsorbable material is produced by polymerization, accordingly the present invention can conduct the separation of a metal zinc catalyst from the material for producing a bioabsorbable material by physical force means such as by peeling-off means or by cutting-off means, and hence the present invention can easily conduct the separation of the metal zinc catalyst. Additionally, the separated catalyst can be converted into a recyclable catalyst by washing with a solvent for the bioabsorbable polymer.

(2) The bioabsorbable material after the removal of the three-dimensionally shaped metal zinc catalyst from the material for producing a bioabsorbable material has a small content of metal zinc even without applying any particular purification treatment; additionally a metal zinc catalyst is used as the catalyst in place of a tin compound having a strong toxicity to living organisms such as tin octylate; and hence the concerned bioabsorbable material is molded by usual molding means into, for example, chips and the chips can be used as a bioabsorbable material in an intended shape such as a membrane-like shape or a film-like shape.

(3) As has been described in above Examples, the three-dimensionally shaped metal zinc catalyst is higher in catalytic activity as compared to heretofore known powdery metal zinc catalysts, and enables the reduction of the polymerization time of the bioabsorbable polymer and the use of low-reactivity components as the components constituting the bioabsorbable polymer.

The invention claimed is:

1. A process for producing a bioabsorbable material, the method comprising:
    polymerizing lactide monomers and ε-caprolactone monomers simultaneously under a three-dimensionally shaped metal zinc polymerization catalyst to provide a bioabsorbable material; and
    removing the three-dimensionally shaped metal zinc polymerization catalyst from the bioabsorbable material by using a physical force,
    wherein the three-dimensionally shaped metal zinc polymerization catalyst has a shape selected from the group consisting of a wire-like shape, a rod-like shape, a plate-like shape, a ball-like shape, a net-like shape, and a mesh-like shape,
    wherein the lactide is at least one selected from the group consisting of L, L-lactide, D, D-lactide, and D, L-lactide, and
    wherein the physical force is a force to peel-off or cut-off the three-dimensionally shaped metal zinc polymerization catalyst.

2. The process according to claim 1, which produces the bioabsorbable material which consists essentially of lactide and ε-caprolactone.

3. The process according to claim 1, wherein the shape of the three-dimensionally shaped metal zinc polymerization catalyst is one of the wire-like shape or the plate-like shape.

* * * * *